(12) United States Patent
Rabovsky et al.

(10) Patent No.: US 9,034,399 B2
(45) Date of Patent: May 19, 2015

(54) DIETARY COMPOSITIONS FOR PROMOTING BRAIN HEALTH

(75) Inventors: Alexander B. Rabovsky, Idaho Falls, ID (US); Jennifer Kelsey, Ririe, ID (US); Jeremy Ivie, Ammon, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 1122 days.

(21) Appl. No.: 12/348,195

(22) Filed: Jan. 2, 2009

(65) Prior Publication Data

US 2009/0175968 A1 Jul. 9, 2009

Related U.S. Application Data

(60) Provisional application No. 61/018,817, filed on Jan. 3, 2008.

(51) Int. Cl.
| | | |
|---|---|---|
| *A61K 36/16* | (2006.01) | |
| *A61K 36/00* | (2006.01) | |
| *A61K 31/70* | (2006.01) | |

(52) U.S. Cl.
CPC .............. *A61K 36/16* (2013.01); *A61K 31/70* (2013.01)

(58) Field of Classification Search
None
See application file for complete search history.

(56) References Cited

U.S. PATENT DOCUMENTS 7,226,916 B1 * 6/2007 Kiliaan et al. ................. 514/165

OTHER PUBLICATIONS

Grundman, Vitamin E and Alzheimer disease: the basis for additional clinical trials, Am J. Clin Nur 2000; 71 (suppl): 630S-6S.*
Crook et al, Effects of phosphatidylserine in alzheimer's disease, Psychopharmacology bulletin, 1992; 28 (1): 61-6.*
Christen, Free radicals in brain pathophysiology, Edited by Giuseppe Poli et al, Dekker New York, 200: 411-425, Effects of *Ginkgo biloba* extract (EGB 761).*

* cited by examiner

*Primary Examiner* — Qiuwen Mi
(74) *Attorney, Agent, or Firm* — Fish & Richardson P.C.

(57) ABSTRACT

Dietary compositions are disclosed herein. For example, dietary compositions containing a combination of a phosphatidylserine, DHA, EPA, antioxidants, and *Ginkgo Biloba* are provided.

12 Claims, No Drawings ically of between about 100 and about 1000 mg of phosphatidylserine complex, between about 17 and about 130 mg of DHA, between about 17 and about 130 mg of EPA, between about 4 and about 90 mg of *Ginkgo Biloba*, and between 4 and 90 mg of antioxidants. In some cases, the antioxidant can include vitamin E. For example, a dietary composition provided herein can include an amount of Vitamin E that provides between about 1 and about 50 IUs of Vitamin E.

DIETARY COMPOSITIONS FOR PROMOTING BRAIN HEALTH

CROSS-REFERENCE TO RELATED APPLICATIONS

This application claims the benefit of U.S. Provisional Application No. 61/018,817, entitled "Dietary Compositions" and filed on Jan. 3, 2008, which is incorporated herein by reference in its entirety.

BACKGROUND

1. Technical Field

This disclosure relates to dietary compositions that promote brain health. For example, this disclosure provides dietary compositions containing phosphatidylserine, at least one omega-3 fatty acid, at least one antioxidant source, and *Ginkgo Biloba*.

2. The Relevant Technology

Dietary compositions can include foods, medicinal ingredients, extracts, herbs, and other forms of matter that can be ingested or otherwise absorbed by some part of the human body. As humans grow older, often times brain activity slows, memory can become impaired, and the brain takes longer to process information. Of course, most people would enjoy the ability to maintain a higher level of cognitive ability in their senior years if given the opportunity. In some cases, early onset of brain dysfunction or slowing can occur even in healthy, young adults and children, often resulting from disease or hereditary biological defects.

BRIEF SUMMARY

In general, this disclosure provides dietary compositions. The dietary compositions provided herein can be used to maintain optimal brain function and health. For example, this disclosure provides dietary compositions containing phosphatidylserine, at least one omega-3 fatty acid, for example docosahexaenoic acid (DHA) and/or eicosapentaenoic acid (EPA), antioxidants, and *Ginkgo Biloba*.

In general, one aspect of this document features a dietary composition comprising phosphatidylserine, DHA, EPA, antioxidants, and *Ginkgo Biloba*. The phosphatidylserine can be present from about 2 percent to about 20 percent by weight. The DHA can be present from about 2 percent to about 15 percent by weight. The EPA can be present from about 2 percent to about 15 percent by weight. The antioxidants can be present from about 0.5 percent to about 10 percent by weight. The *Ginkgo Biloba* can be present from about 0.5 percent to about 10 percent by weight. The dietary composition can be administered in any suitable form, for example as a pill, a powder, or a liquid.

In another aspect, this document features a dietary composition consisting of between 17 and 170 mg of phosphatidylserine, between 17 and 130 mg of DHA, between 17 and 130 mg of EPA, between 4 and 90 mg of antioxidants, and between 4 and 90 mg of *Ginkgo Biloba*. In another aspect, this document features a dietary composition consisting essentially of between 17 and 170 mg of phosphatidylserine, between 17 and 130 mg of DHA, between 17 and 130 mg of EPA, between 4 and 90 mg of antioxidants, and between 4 and 90 mg of *Ginkgo Biloba*.

In another aspect, this document features a dietary composition consisting of between about 100 and about 1000 mg of phosphatidylserine complex, between about 17 and about 130 mg of DHA, between about 17 and about 130 mg of EPA, between about 4 and about 90 mg of *Ginkgo Biloba*, and between 4 and 90 mg of antioxidants. In another aspect, this document features a dietary composition consisting essentially of between about 100 and about 1000 mg of phosphatidylserine complex, between about 17 and about 130 mg of DHA, between about 17 and about 130 mg of EPA, between about 4 and about 90 mg of *Ginkgo Biloba*, and between 4 and 90 mg of antioxidants. In some cases, the antioxidant can include vitamin E. For example, a dietary composition provided herein can include an amount of Vitamin E that provides between about 1 and about 50 IUs of Vitamin E.

In another aspect, this document features a dietary composition consisting of about 500 mg of phosphatidylserine complex, about 60 mg of DHA, about 60 mg of EPA, and an amount of Vitamin E that provides about 10 IUs of Vitamin E. In another aspect, this document features a dietary composition consisting essentially of about 500 mg of phosphatidylserine complex, about 60 mg of DHA, about 60 mg of EPA, and an amount of Vitamin E that provides about 10 IUs of Vitamin E.

In another aspect, this document features a dietary supplement for maintaining brain health, the supplement comprising effective amount of two different omega-3-fatty acids, a phospholipid, an antioxidant, a flavonoid, and a glycoside. One of the omega-3-fatty acids can be EPA. One of the omega-3 fatty acids can be DHA. The phospholipid can be phosphatidylserine. The phospholipid can be phosphatidylcholine. The antioxidant can be D-alpha-tocopherol or other Vitamin E. The flavonoid can be a blueberry extract or a *Ginkgo Biloba* extract. The glycoside can be a *Ginkgo Biloba* extract.

Unless otherwise defined, all technical and scientific terms used herein have the same meaning as commonly understood by one of ordinary skill in the art to which this disclosure pertains. Although methods and materials similar or equivalent to those described herein can be used in the practice or testing, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments are set forth in the description below. Other features, objects, and advantages will be apparent from the detailed description, and from the claims.

DETAILED DESCRIPTION OF CERTAIN EMBODIMENTS

In general, this disclosure provides dietary compositions for improving brain health. For example, this disclosure provides dietary compositions containing phosphatidylserine, the omega-3-fatty acids DHA and/or EPA, antioxidants, and *Ginkgo Biloba*.

Any form of phosphatidylserine can be included in a dietary composition provided herein. In general, phosphatidylserine can be a phospholipid found in most cells of the body, particularly in the brain. Phosphatidylserine is a phospholipid nutrient found in fish, green leafy vegetables, soybeans, and rice. Phosphatidylserine can slow or even reverse the effects of age-related cognitive degeneration.

A dietary composition provided herein can contain any amount of phosphatidylserine. For example, a dietary composition can contain from 0.01 µg to about 1 g (e.g., from about 0.01 µg to about 750 mg; from about 0.01 µg to about 500 mg; from about 0.1 µg to about 1 g; from about 1 µg to about 1 g; from about 10 µg to about 1 g; or from about 100 µg to about 500 mg) of phosphatidylserine. In some cases, a dietary composition can contain about 10, 20, 30, 40, 50, 60, 70, 80, 90, 100, 110, 120, 130, 140, 150, 160, 170, 180, 190, 200, 210, 220, 230, 240, 250, 300, 400, 500, 600, 700, 800, 900, 1000 mg or more of phosphatidylserine, about any amount of phosphatidylserine between these enumerated amounts, or any range of phosphatidylserine amounts encompassing one or more of these enumerated amounts (e.g., from about one of the enumerated amounts of phosphatidylserine to about another of the enumerated amounts of phosphatidylserine). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary composition can be phosphatidylserine. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of phosphatidylserine, about any percentage of phosphatidylserine between these enumerated percentages, or any range of phosphatidylserine percentages encompassing one or more of these enumerated percentages (e.g., from about one of the enumerated percentages of phosphatidylserine to about another of the enumerated percentages of phosphatidylserine).

In some cases, phosphatidylserine can be provided in a dietary composition as substantially pure phosphatidylserine. As used herein, the term "substantially pure" refers to a compound having a purity greater than about 90% based on the weight of the compound, e.g., greater than about 90, 91, 92, 93, 94, 95, 96, 97, 98, and 99% pure by weight, including a compound that is about 100% pure by weight. In some cases, phosphatidylserine can be provided in a dietary composition as part of a complex (e.g., a complex that contains phosphatidylserine in addition to one or more other components). Phosphatidylserine can be in any form, for example, a solution, a powder, or a soluble powder.

Certain embodiments of the invention include at least one omega-3 fatty acid source. One non-limiting omega-3 fatty acid source is docosahexaenoic acid (DHA). For example, a dietary composition can include DHA. DHA is an omega-3 fatty acid found commonly in cold-water fish. DHA is a carboxylic acid with a 22-carbon chain. DHA can be in any form, for example, a solution, a powder, or a soluble powder.

A dietary composition provided herein can contain any type or derivative of DHA. Any appropriate method can be used to obtain DHA. For example, extraction can be used to obtain a preparation of DHA. In some cases, DHA can be extracted from naturally-occurring sources. In some cases, a liquid-liquid extraction process can be performed using fish oil as a source material to obtain a preparation of DHA. A dietary composition provided herein can contain any amount of DHA. For example, a dietary composition can contain from 0.01 µg to about 2 g (e.g., from about 0.01 µg to about 2 g; from about 0.01 µg to about 1 g; from about 0.1 µg to about 750 mg; from about 1 µg to about 500 mg; from about 10 µg to about 1 g; or from about 100 µg to about 750 mg) of DHA. In some cases, a dietary composition can contain about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 mg or more of DHA, about any amount of DHA between these enumerated amounts, or any range of DHA amounts encompassing one or more of these enumerated amounts (e.g., from about one of the enumerated amounts of DHA to about another of the enumerated amounts of DHA). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary composition can be DHA. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of DHA, about any percentage of DHA between these enumerated percentages, or any range of DHA percentages encompassing one or more of these enumerated percentages (e.g., from about one of the enumerated percentages of DHA to about another of the enumerated percentages of DHA).

Another non-limiting omega-3 fatty acid source is eicosapentaenoic acid (EPA). EPA is an omega-3 fatty acid found commonly in cold-water fish. EPA is a carboxylic acid with a 22-carbon chain (all-cis-5,8,11,14,17-eicosapentaenoic acid). EPA can be in any form, for example, a solution, a powder, or a soluble powder.

A dietary composition provided herein can contain any type or derivative of EPA. Any appropriate method can be used to obtain EPA. For example, extraction can be used to obtain a preparation of EPA. In some cases, EPA can be extracted from naturally-occurring sources. In some cases, a liquid-liquid extraction process can be performed using fish oil as a source material to obtain a preparation of EPA. A dietary composition provided herein can contain any amount of EPA. For example, a dietary composition can contain from 0.01 µg to about 2 g (e.g., from about 0.01 µg to about 2 g; from about 0.01 µg to about 1 g; from about 0.1 µg to about 750 mg; from about 1 µg to about 500 mg; from about 10 µg to about 1 g; or from about 100 µg to about 750 mg) of EPA. In some cases, a dietary composition can contain about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 mg or more of EPA, about any amount of EPA between these enumerated amounts, or any range of EPA amounts encompassing one or more of these enumerated amounts (e.g., from about one of the enumerated amounts of EPA to about another of the enumerated amounts of EPA). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary composition can be EPA. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of EPA, about any percentage of EPA between these enumerated percentages, or any range of EPA percentages encompassing one or more of these enumerated percentages (e.g., from about one of the enumerated percentages of EPA to about another of the enumerated percentages of EPA).

In some cases, a dietary composition provided herein can include DHA, EPA, or both, wherein the DHA, EPA, or both are provided as components of another ingredient. For example, a dietary composition provided herein can contain an oil, which oil contains DHA, EPA, or both. In some cases, such oil can be fish oil, e.g., derived from cold-water fish. In some cases, a dietary composition can contain about 100, 110, 120, 130, 140, 150, 160, 170, 180, 190, 200, 210, 220, 230, 240, 250, 260, 270, 280, 290, 300, 31, 320, 330, 340, 350, 360, 370, 380, 390, 400, 410, 420, 430, 440, 450, 460, 470, 480, 490, 500 mg or more of fish oil, about any amount of fish oil between these enumerated amounts, or any range of fish oil amounts encompassing one or more of these enumerated amounts (e.g., from about one of the enumerated amounts of fish oil to about another of the enumerated amounts of fish oil).

Certain embodiments of the invention include at least one antioxidant source. An antioxidant can be any molecule capable of slowing or preventing the oxidation of another molecule. Any type of antioxidant can be included in a dietary composition provided herein. Examples of antioxidants include, without limitation, flavonoid, flavongycoside, anthocyanin, tocopherol, D-alpha-tocopherol or other Vitamin E, tocoptrienol, and carotenoid antioxidants. Antioxidants can be in any form, for example, a solution, a powder, or a soluble powder. In some cases, a dietary composition provided herein can contain an antioxidant in an amount that provides a particular potency when ingested. As one non-limiting example, International Units or "IUs" are used as a standard measure of potency. In some cases, a dietary composition provided herein can contain an antioxidant in an amount that provides about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more IUs, an antioxidant in about any amount that provides an IU between these enumerated IUs, or any range of amounts of antioxidants that provides an IU encompassing one or more of these enumerated IUs (e.g., from about one amount that provides one of the enumerated IUs to about another amount that provides another of the enumerated IUs).

A dietary composition provided herein can contain any number of different antioxidants. For example, a dietary composition can contain one, two, three, four, five, six, seven, eight, nine, ten, or more different antioxidants. Any appropriate method can be used to obtain antioxidants. For example, extraction can be used to obtain a preparation of antioxidants. In some cases, antioxidants can be extracted from naturally-occurring sources, such as plants. In particular, *Ginkgo Biloba* and blueberry can be used as sources of antioxidants. In some cases, a solid phase extraction process can be performed using *Ginkgo Biloba* leafs as a source material to obtain a preparation of antioxidant. In some cases, an antioxidant to be included in dietary compositions provided herein can be derived from blueberry skin. A dietary composition provided herein can contain any amount of an antioxidant. For example, a dietary composition can contain from 0.01 µg to about 0.5 g (e.g., from about 0.01 µg to about 250 mg; from about 0.01 µg to about 100 mg; from about 0.1 µg to about 50 mg; from about 1 µg to about 500 mg; from about 10 µg to about 500 mg; or from about 100 µg to about 500 mg) of antioxidant. In some cases, a dietary composition can contain about 1, 2, 3, 4, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 mg or more of an antioxidant, about any amount of antioxidant between these enumerated amounts, or any range of antioxidant amounts encompassing one or more of these enumerated amounts (e.g., from about one of the enumerated amounts of antioxidant to about another of the enumerated amounts of antioxidant). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary composition can be antioxidants. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of an antioxidant, about any percentage of antioxidant between these enumerated percentages, or any range of antioxidant amounts encompassing one or more of these enumerated percentages (e.g., from about one of the enumerated percentages of antioxidant to about another of the enumerated percentages of antioxidant).

Certain embodiments of the invention also include *Ginkgo Biloba*. *Ginkgo Biloba* can include any species of tree contained within the genus *Ginkgo*. *Ginkgo Biloba* is also known as the Maidenhair Tree. Any type of *Ginkgo Biloba* can be included in a dietary composition provided herein. In some cases, *Ginkgo Biloba* extract can be provided in a dietary composition. In some case, a *Ginkgo Biloba* extract can be obtained from a *Ginkgo Biloba* leaf. *Ginkgo Biloba* can be in any form, for example, a solution, a powder, or a soluble powder.

In general, extraction is a process whereby the desired constituents of a source material (e.g., a fruit, vegetable, plant, or plant part) are removed using, for example, a solvent. To produce an extract, fruit, vegetable, plant, or plant part material can be first cleaned and dried, if necessary. Drying can be performed naturally (e.g., by air drying) or artificially (e.g., using warm-air fans or conveyor dryers). Fruit, vegetable, plant, or plant part material can then be ground, cut, or shredded using, for example, hammer action, pressure, friction, or impact cutting. Methods of removing the desired constituents from the plant material include, without limitation, organic solvent extraction, supercritical gas extraction, and steam distillation.

The ability to use a number of different solutes, diluents, extractants, and aqueous phases as well as rapid extraction kinetics for many separations, can make solvent extraction a powerful separation method. By way of example, there are a number of procedures for organic solvent extraction, including maceration (soaking and agitating the fruit, vegetable, plant, or plant part material with a solvent), percolation (repeated rinsing of the fruit, vegetable, plant, or plant part material with a solvent), and countercurrent extraction (continuous flow of a solvent in the opposite direction as the fruit, vegetable, plant, or plant part material).

Representative solvents include, without limitation, water, methanol, hexane, ethanol, benzene, toluene, and ether. Aqueous extracts, such as decoctions (produced by boiling the fruit, vegetable, plant, or plant part material such as hard tissues), infusions (produced by steeping the fruit, vegetable, plant, or plant part material such as soft tissues), or macerations, can also be produced. In some cases, numerous separation procedures can be used to further purify desired components or remove unwanted or contaminating components. Examples of such separation procedures include, without limitation, decanting, filtration, sedimentation, centrifugation, heating, adsorption, precipitation, chromatography, or ion exchange. The resulting products can be subsequently evaporated, vaporized, lyophilized, spray dried, freeze-dried, or vacuum dried.

In some cases, a dietary composition provided herein can contain one or more radical scavengers, antioxidants, reducing agents, or mixtures thereof. For example, a dietary composition provided herein can contain one or more radical scavengers, antioxidants, reducing agents, or mixtures thereof in an amount that effectively reduces oxidation or degradation of other ingredients present within the composition. Examples of radical scavengers and antioxidants include, without limitation, ascorbic acid, flavonoids, flavongycosides, anthocyanins, tocopherols, D-alpha-tocopherol or other Vitamin E, tocoptrienols, and carotenoids, and butyl hydroxytoluene. Sodium bisulfite is an example of a reducing agent that can be incorporated into a dietary composition.

In some cases, a dietary composition provided herein can contain phosphatidylserine, DHA, EPA, antioxidants, and *Ginkgo Biloba*. The weight ratio of phosphatidylserine to other, optional ingredients (e.g., DHA, EPA, antioxidants, *Ginkgo Biloba*, and other additives) can be from about 1:20 to about 4:1. The ratio can be based, for example, on the dry weight of each ingredient or extract.

In some cases, a dietary composition provided herein can be designed to contain the following: 60 mg of DHA, 60 mg of EPA, 100 mg of phosphatidylserine, 40 mg of *Ginkgo Biloba* extract, 17 mg of blueberry powder, 6.7 mg of α-tocopherol, and 14 mg of phosphatidylcholine.

A dietary composition provided herein can be ingested. For example, a dietary composition can be administered orally or intragastrically. In some cases, a dietary composition provided herein can be administered by other routes such as nasally, intravenously, intramuscularly, subcutaneously, sublingually, intrathecally, or intradermally. Any amount of a dietary composition provided herein can be administered to a mammal. The dosages of a dietary composition can depend on many factors, including the mode of administration. The amount of phosphatidylserine, DHA, EPA, antioxidants, and *Ginkgo Biloba* contained within a single dose of a dietary composition can be an amount that can effectively maintain a desired result in a mammal without inducing significant toxicity. For example, a dietary composition can be formulated in a dose such that an individual receives from about 10 mg up to about 1000 mg of phosphatidylserine, from about 10 mg up to about 2000 mg of DHA, from about 10 mg up to about 2000 mg of EPA, from about 1 mg up to about 500 mg of antioxidants, from about 5 mg up to about 200 mg of *Ginkgo Biloba*, per day.

A dietary composition provided herein can be in the form of a liquid, solution, suspension, pill, capsule, tablet, gelcap, powder, or gel. For oral administration, tablets or capsules can be prepared by conventional means with acceptable excipients such as binding agents, fillers, lubricants, disintegrants, or wetting agents. The tablets can be coated, if desired. Liquid preparations for oral administration can take the form of, for example, solutions, syrups, or suspension, or they can be presented as a dry product for constitution with saline or other suitable liquid vehicle before use. Dietary compositions of the type described herein also can contain acceptable additives such as suspending agents, emulsifying agents, non-aqueous vehicles, preservatives, buffer salts, flavoring, coloring, and sweetening agents as appropriate. Dietary composition of the type described herein can contain one or more additional additives including, but not limited to, gelatin, glycerin, water, beeswax, lecithin, cocoa, caramel, titanium dioxide, or carmine. Preparations for oral administration also can be suitably formulated to give controlled release of the ingredients.

In some cases, the dietary composition can be in the form of a softgel. Softgels are predominantly used to contain liquids containing one or more active ingredients in a dissolved or suspended state. Use of softgel formulations can enhanced bioavailability of one or more active ingredients resulting from the fact that the pharmaceutical already in solution at the site of absorption, thereby permitting faster and more uniform absorption to occur. Softgels can be provided with suitable coatings which typically contain gelatin and/or suitable edible dye(s). In some cases, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies. In some cases, flavoring may be added to the softgel coat to enhance the taste.

In some cases, a dietary composition provided herein can contain an acceptable carrier for administration to a mammal (e.g., a human), including, without limitation, sterile aqueous, or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration.

As described herein, a dietary composition can be used for promoting brain health in a mammal. Brain health can be examined using any appropriate method. For example, by measuring cognitive ability using standardized tests. Other examples of measuring cognitive ability include test for recall items, details, dates, and telephone numbers. A human's cognitive ability can be continually or intermittently monitored over a period of time, e.g., once a day, once a week, once a month. A trend may indicate the effectiveness of a dietary composition in maintaining or increasing a human's cognitive ability or maintaining brain health.

In some cases, the dietary composition can be in the form of a shake or bar. For example, a blend of ingredients provided herein can be incorporated into a base of soy crisps, syrups, sweeteners, and fiber sources to produce an extruded protein bar. In some cases, the product can be in the form of a chocolate bar (e.g., a chocolate protein bar) of substantially uniform consistency. The chocolate bar can be dark chocolate, light chocolate, white chocolate, any other type of chocolate, or a mixture thereof. For example, a dietary composition can be in the form of a dark chocolate bar. Dark chocolate is known to contain cacao, a substance known to contain over 300 identifiable compounds including protein, fiber, iron, zinc, copper, calcium, magnesium, and high levels of potent antioxidants. Optionally, caramel, peanut butter, or any of a variety of other flavorings or food products can be added to the bar. A bar can be, for example, about 50 grams in weight, and can provide one serving of pre-blend. A bar can be of greater or lesser weight (e.g., 25 or 100 grams), and can provide more or less and one serving of pre-blend (e.g. half a serving or two servings). The product can be coated or partially coated in chocolate (or other flavor), and each bar can be individually packaged. The product can be coated or partially coated in dark chocolate, light chocolate, any other type of chocolate, or a mixture thereof. The final product can be consumed as one serving as either a meal replacement or snack item. In another example, a blend of ingredients provided herein can be added to a meal replacement shake base (including fructose, sunflower oil creamer, protein, and fiber sources to create a meal replacement shake that includes one serving of pre-blend). The final shake can be any flavor (e.g., chocolate, vanilla, or strawberry). Final serving size can be, for example, 30 g to be dispersed into 8 ounces of milk or water (or other suitable liquid) to form one complete serving. Final serving size can be greater or lesser than 30 grams (e.g., 15 or 60 grams) and can provide more or less than one complete serving (e.g., half a serving or two servings).

In some cases, dietary compositions provided herein can be provided to a subject for ingestion as softgels, in addition to being provided as shakes or bars, to increase the amount of phosphatidylserine, DHA, EPA, antioxidants, *Ginkgo Biloba*, or any other ingredients in the dietary composition consumed by the subject.

The following examples further describe dietary compositions but do not limit the scope of the inventive concepts described in the claims.

EXAMPLES

Example 1

Dietary Composition Formulation

Phosphatidylserine, DHA, EPA, antioxidants, and *Ginkgo Biloba* were used to create a mixture. The mixture was blended and encapsulated in soft gelatin capsule form to provide a dietary composition containing 12% by weight phosphatidylserine, 7% by weight DHA, 7% by weight EPA, 2.8% by weight antioxidants, and 4.7% by weight *Ginkgo Biloba*.

Example 2

Dietary Composition Formulation

Phosphatidylserine, DHA, EPA, antioxidants, and *Ginkgo Biloba* were used to create a mixture. The mixture was blended and incorporated into a consumable chocolate form to provide a dietary composition containing 12% by weight phosphatidylserine, 7% by weight DHA, 7% by weight EPA, 2.8% by weight antioxidants, and 4.7% by weight *Ginkgo Biloba*. The blend was incorporated into a chocolate base to create a chocolate bar (molded) that contains one serving of described mixture. This product can be consumed as one serving, for example, in lieu of one serving of a capsule, gelcap, or tablet of product.

Example 3

Dietary Composition Formulation

Phosphatidylserine, DHA, EPA, antioxidants, and *Ginkgo Biloba* were used to create a mixture. The mixture was blended and encapsulated in soft gelatin capsules form to provide a dietary composition containing 3.5% by weight phosphatidylserine, 11.7% by weight DHA, 10.5% by weight EPA, 4.7% by weight antioxidants, and 2.9% by weight *Ginkgo Biloba*.

Example 4

Dietary Composition Formulation

Phosphatidylserine, DHA, EPA, antioxidants, and *Ginkgo Biloba* were used to create a mixture. The mixture was blended and incorporated into a consumable chocolate form to provide a dietary composition containing 3.5% by weight phosphatidylserine, 11.7% by weight DHA, 10.5% by weight EPA, 4.7% by weight antioxidants, and 2.9% by weight *Ginkgo Biloba*.

Other Embodiments

It is to be understood that while the above embodiments have been described in conjunction with the detailed description thereof, the foregoing description is intended to illustrate, and not limit the scope of the inventive concepts, which are defined by the scope of the appended claims. Other aspects, advantages, and modifications are within the scope of the following claims.

What is claimed is:

1. A dietary supplement capsule consisting of between about 100 and about 1000 mg of phosphatidylserine complex, fish oil comprising between about 17 and about 130 mg of docosahexaenoic acid and between about 17 and about 130 mg of eicosapentaenoic acid, between about 4 and about 90 mg of *Ginkgo Biloba*, between 4 and 90 mg of Vitamin E, a blueberry extract, phosphatidylcholine, and one or more of gelatin, glycerin, water, beeswax, lecithin, cocoa, caramel, titanium dioxide, and a coloring agent.

2. The dietary supplement capsule of claim 1, wherein said Vitamin E provides about 10 IUs of Vitamin E.

3. The dietary supplement capsule of claim 1, wherein said phosphatidylserine complex in said dietary supplement capsule is present in an amount of about 500 mg, wherein said docosahexaenoic acid is present in an amount of about 60 mg, wherein said eicosapentaenoic acid is present in an amount of about 60 mg, and wherein said Vitamin E is present in an amount that provides about 10 IUs of Vitamin E.

4. The dietary supplement capsule of claim 3, wherein the phosphatidylserine complex includes about 25 to about 200 mg of pure phosphatidylserine.

5. The dietary supplement capsule of claim 3, wherein the phosphatidylserine complex includes about 100 mg of pure phosphatidylserine.

6. The dietary supplement capsule of claim 1, wherein said coloring agent is carmine.

7. A dietary supplement capsule consisting of about 100 mg of phosphatidylserine complex, fish oil comprising between about 60 mg of docosahexaenoic acid and about 60 mg of eicosapentaenoic acid, about 40 mg of *Ginkgo Biloba*, about 17 mg of blueberry powder, between 4 and 90 mg of d-alpha tocopherol, and about 14 mg of phosphatidylcholine, and one or more of gelatin, glycerin, water, beeswax, lecithin, cocoa, caramel, titanium dioxide, and a coloring agent.

8. The dietary supplement capsule of claim 7, wherein said dietary supplement capsule comprises about 6.7 mg of d-alpha tocopherol.

9. The dietary supplement capsule of claim 7, wherein said coloring agent is carmine.

10. A dietary supplement capsule consisting of about 100 mg of phosphatidylserine complex, fish oil comprising between about 60 mg of docosahexaenoic acid and about 60 mg of eicosapentaenoic acid, about 40 mg of *Ginkgo Biloba*, about 17 mg of blueberry powder, between 4 and 90 mg of Vitamin E, and about 14 mg of phosphatidylcholine, and one or more of gelatin, glycerin, water, beeswax, lecithin, cocoa, caramel, titanium dioxide, and a coloring agent.

11. The dietary supplement capsule of claim 10, wherein said Vitamin E provides about 10 IUs of Vitamin E.

12. The dietary supplement capsule of claim 10, wherein said coloring agent is carmine.

* * * * *